(12) United States Patent
Kim et al.

(10) Patent No.: US 6,391,173 B1
(45) Date of Patent: May 21, 2002

(54) ELECTROCHEMICAL CORROSION POTENTIAL SENSOR

(75) Inventors: Young-Jin Kim, Clifton Park, NY (US); Prodyot Roy, Saratoga, CA (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/426,710

(22) Filed: Oct. 25, 1999

(51) Int. Cl.[7] .................. G01N 17/04; G01N 27/30; G21C 17/00
(52) U.S. Cl. ............... 204/404; 204/400; 205/775.5; 376/245; 376/305
(58) Field of Search ................ 204/404, 400; 205/775.5; 376/295, 305

(56) References Cited

U.S. PATENT DOCUMENTS

| | | | |
|---|---|---|---|
| 5,130,081 A | | 7/1992 | Niedrach ............... 376/305 |
| 5,192,414 A | * | 3/1993 | Indig et al. ............. 204/400 |
| 5,217,596 A | * | 6/1993 | Indig et al. ............. 204/435 |
| 5,238,553 A | | 8/1993 | Hettiarachchi et al. ..... 204/435 |
| 5,465,281 A | * | 11/1995 | Andresen et al. ......... 376/305 |
| 5,571,394 A | * | 11/1996 | Hettiarachchi et al. ..... 204/400 |
| 5,848,113 A | | 12/1998 | Kim et al. ............... 376/305 |
| 6,181,760 B1 | * | 1/2001 | JinKim ................... 376/245 |

OTHER PUBLICATIONS

Marks et al., "Standard Handbook for Mechanical Engineers", pp. 6–36–37, month N/A 1987.*

"Corrosion Potential Behaviour in High–Temperature Water of Noble Metal–Doped Alloy Coatings Deposited by Underwater Thermal Spraying," Kim, Y.–J., Andresen, P.L., Gray, D.M., Lau, Y.–C., and Offer, H.P. Corrosion 52 (6) 440–446 (1996). Month N/A.

"Noble Metal Coating Development for Shroud Stress Corrosion Crack Mitigation," GE Nuclear Energy Report NEDC–32257C, Class 2, Mar. 1995.

* cited by examiner

Primary Examiner—Robert J. Warden, Sr.
Assistant Examiner—Kaj K. Olsen
(74) Attorney, Agent, or Firm—Robert P. Santandrea; Noreen C. Johnson

(57) ABSTRACT

An electrochemical corrosion potential sensor includes a ceramic tip insulating member, and a sensor tip joined to the ceramic tip insulating member, the sensor tip comprising an alloy. Further, a coating is provided on an outer surface of the sensor tip, the coating including a noble metal, and a conductor electrically connected to said sensor tip.

17 Claims, 1 Drawing Sheet

ELECTROCHEMICAL CORROSION POTENTIAL SENSOR

BACKGROUND OF THE INVENTION

Nuclear reactors are typically in the form of a boiling water reactor having suitable nuclear fuel disposed in a reactor pressure vessel in which water is heated. The water and steam are carried through various components and piping which are typically formed of stainless steel, with other materials such as alloy 182 weld metal and alloy 600 being used for various components directly inside the reactor pressure vessel.

Materials in the reactor core region are susceptible to irradiation assisted stress corrosion cracking. This is because the material in the core region is exposed to the highly oxidizing species generated by the radiolysis of water by both gamma and neutron radiation under normal water chemistry conditions, in addition to the effect of direct radiation assisted stress corrosion cracking. The oxidizing species increases the electrochemical corrosion potential of the material which in turn increases its propensity to undergo intergranular stress corrosion cracking or irradiation assisted stress corrosion cracking.

Suppression of the oxidizing species carried within such materials is desirable in controlling intergranular stress corrosion cracking. An effective method of suppressing the oxidizing species coming into contact with the material is to inject hydrogen into the reactor water via the feedwater system so that recombination of the oxidants with hydrogen occurs within the reactor circuit.

This method is called hydrogen water chemistry and is widely practiced for mitigating intergranular stress corrosion cracking of materials in boiling water reactors. When hydrogen water chemistry is practiced in a boiling water reactor, the electrochemical corrosion potential of the stainless steel material decreases from a positive value generally in the range of 0.050 to 0.200 V (SHE) under normal water chemistry to a value less than -0.230 V (SHE), where SHE stands for the Standard Hydrogen Electrode potential. When the electrochemical corrosion potential is below this negative value, intergranular stress corrosion cracking of stainless steel can be mitigated and its initiation can be prevented.

Considerable efforts have been made in the past decade to develop reliable electrochemical corrosion potential sensors to be used as reference electrodes which can be used to determine the electrochemical corrosion potential of operating surfaces of components.

The typical electrochemical corrosion potential sensor experiences a severe environment in view of the temperature of the water well exceeding 88° C.; relatively high flow rates of the water up to and exceeding several m/s; and the high nuclear radiation in the core region.

A drawback of currently available sensors is that they have a limited lifetime in that some have failed after only three months of use while a few have shown evidence of operation for approximately six to nine months. Two major modes of sensor failure have been the cracking and corrosive attack in a ceramic-to-metal braze used at the sensing tip, and the dissolution of a sapphire insulating ceramic material used to electrically isolate the sensing tip from the metal conductor cable for platinum and stainless steel type sensors.

The electrochemical corrosion potential sensors may be mounted either directly in the reactor core region for directly monitoring electrochemical corrosion potential of in-core surfaces, or may be mounted outside the reactor core to monitor the electrochemical corrosion potential of out-of-core surfaces. However, the typical electrochemical corrosion potential sensor nevertheless experiences a severe operating environment in view of: the high temperature of water (typically from 250 to 300° C. during operation and from 100 to 150° C. during shut down); relatively high flowrates of the water up to and exceeding several m/s; and due to the high nuclear radiation in the core region. This complicates the design of the sensor since suitable materials are required for this hostile environment, and must be suitably configured for providing a water-tight assembly for a suitable useful life.

Corrosion tests in high velocity water have shown that MgO ("magnesia"), $Y_2O_3$ ("yttria") or CaO (Calcia) stabilized $ZrO_2$ ("zirconia") ("MSZ", "YSZ" or "CSZ" respectively) have a significantly lower corrosion rate than sapphire. Efforts have therefore been made to braze a platinum cap onto a stabilized zirconia insulator. Due to the characteristically high defects associated with stabilized zirconia, it has been found difficult to metallize the stabilized zirconia in order to enable effective brazing of the platinum cap thereto. Furthermore, undesirable alloy formation has been observed between the platinum in the cap and silver in the braze material.

SUMMARY OF THE INVENTION

An electrochemical corrosion potential sensor includes a ceramic tip insulating member, and a sensor tip joined to the ceramic tip insulating member, the sensor tip comprising an alloy. Further, a coating is provided on an outer surface of the sensor tip, the coating including a noble metal, and a conductor electrically connected to said sensor tip. A method for fabricating the electrochemical corrosion potential sensor is also disclosed.

BRIEF DESCRIPTION OF THE DRAWINGS

Preferred embodiments of the invention are described below with reference to the accompanying drawing in which.

DETAILED DESCRIPTION OF THE INVENTION

Figure 1:
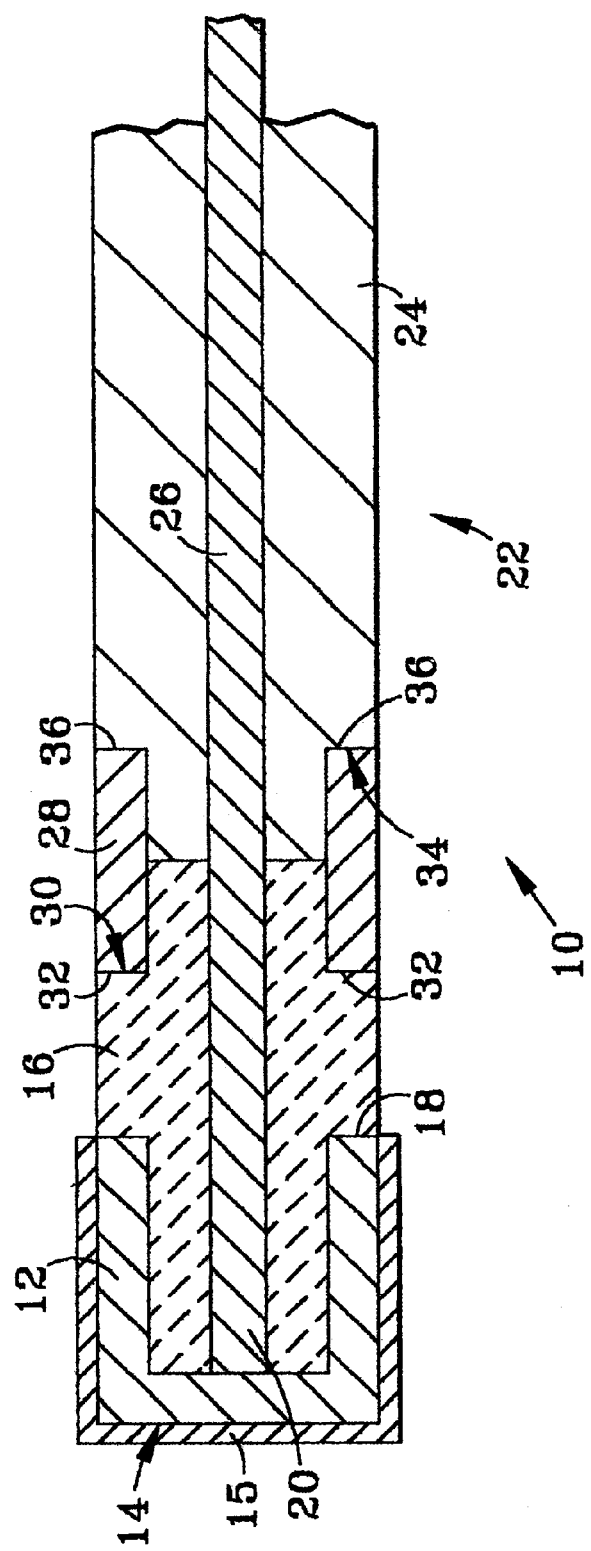
FIG. 1 is a sectional view taken axially along an electrochemical corrosion potential sensor according to the present invention.

An electrochemical corrosion potential sensor ("sensor") according to the present invention is generally illustrated by reference 10 in FIG. 1. The sensor 10 would typically be of generally cylindrical shape however this is not a functional requirement, merely a preference from a manufacturing viewpoint.

The sensor 10 has a cup-shaped tip 12 of alloy 42 (also known as "invar") which is a 36% Ni - 64% Fe alloy, or alternatively of "kovar" which is of similar composition to "invar" but having a small amount of cobalt. The tip 12 is coated on an outer surface 14 with a coating 15 of noble metal containing powders. The coating 15 may be applied to the tip 12 by thermal spraying the outer surface of the tip 12 with a powder of iron and nickel base alloy containing small amounts of noble metals. Platinum and palladium are two noble metals which have been successfully applied to structural material, such as iron base alloys and nickel base alloys by thermal spraying. It is expected that other noble metals including rhodium, iridium, ruthenium and osmium would also produce satisfactory results. "Small amounts" of noble metals refers to amounts which, when deposited, exhibit a catalytic effect to react oxidants with hydrogen to form water. The reaction kinetics for this reaction are generally quite slow in the absence of a catalyst on the surface requiring a substantial excess of hydrogen. "Catalytic effect" refers to an enhanced reaction rate which, given a high enough noble metal concentration on the surface, allows the aforesaid redox reaction of oxygen radicals with hydrogen to occur when a stoichiometric or near stoichiometric molar ratio (ie; a 2:1 molar ratio or 1:8 weight ratio of hydrogen to oxygen) exists.

Typically, the iron and nickel base alloys will contain from 0.05 to 0.4% by weight of the noble metals depending on the noble metals and the base metals. Nickel base alloys such as alloy 600, alloy 42, and alloy 182 typically work well at about 0.3% by weight palladium but as little as 0.1% rhodium and platinum may be used. Lesser amounts (as low as 0.1 or 0.2% by weight of palladium) will also exhibit some partial catalytic properties but to a less preferential degree. Low alloy steels may require 0.5% by weight palladium.

Although alloy 42 ("invar") or kovar have been found to work well for the sensor tip 12 because of their brazeability to YZS, MZS and CZS, other stainless steels may be used as long as they are capable of forming good, reliable braze joints with the YZS, MZS or CZS tip insulating member 16.

Two thermal spraying techniques which may be used to apply the noble metal containing powder are air plasma spraying ("PS") and hyper-velocity oxy-fuel ("HVOF") techniques. The use of such techniques to apply noble metal alloy coatings to stainless steel is known and is discussed for example in Y.J. Kim et al;, "Corrosion Potential Behaviour in High-Temperature Water of Noble Metal-Doped Alloy Coatings Deposited by Under Water Thermal Spraying", Corrosion, Vol. 52-6, p. 440, 1996. Although the foregoing report deals primarily with type 304 stainless steels, similar techniques may be used with alloy 42 and presumably with other stainless steels. Typical coating thicknesses would be on the order of about 5 to 10 mils (about 0.13 to about 0.25 mm).

A tip insulating member 16 of a ceramic material is sealingly joined to the sensor tip 12. Suitable ceramic materials include yttria, magnesia and calcia stabilized zirconia (YSZ, MSZ and CSZ). The sensor tip 12 and tip insulating member 16 may be sealingly joined by brazing at reference 18 with a suitable brazing alloy such as a silver based active metal.

The sensor tip 12 is electrically connected, by suitable means such as welding, to a conductor 20. The conductor 20 extends from a mineral oxide insulated cable 22 having a mineral oxide insulator 24, typically of alumina but possibly also from YZS or MZS, extending around a stainless steel conductor 26. As illustrated in FIG. 1, the conductor 20 may be an extension of the stainless steel conductor 26 beyond the mineral oxide insulator 24 although a separate conductor extending between and electrically connected to the conductor 26 with the mineral oxide insulated cable 22 and the sensor tip 12 may be used as an alternative.

The mineral oxide insulated cable 22 is joined to the tip insulating member 16 by sleeve 28 typically of alloy 42. The sleeve 28 has a first end 30 which encircles the tip insulating member 16 and is sealingly joined thereto by brazing at reference 32. A second end 34 of the sleeve 28 extends about and is sealingly joined to the mineral oxide insulator 24 by brazing at reference 36. The sleeve 28 is preferably of alloy 42 because of its ability to form good braze joints with the mineral oxide insulator 24 but other alloys such as stainless steels with satisfactory brazing capabilities may be used as an alternative. As the tip insulating member 16 insulates the sensor tip 12 from the sleeve 28, the sleeve 28 must of course be spaced apart from the sensor tip 12.

The above description is intended in an illustrative rather than a restrictive sense. Variations to the representative embodiments described may be apparent to persons skilled in the design and manufacture of such structures without departing from the spirit and scope of the invention as defined by the claims set out below.

We claim:

1. An electrochemical corrosion potential sensor comprising:

a solid ceramic tip insulating member, said ceramic tip insulating member comprising a stabilized zirconia;

a sensor tip joined to the ceramic tip insulating member by a braze, said sensor tip comprising an alloy;

a coating provided on an outer surface of the sensor tip, said coating comprising at least one noble metal and at least one of an iron-base alloy and a nickel-base alloy; and a conductor electrically connected to said sensor tip.

2. An electrochemical corrosion potential sensor according to claim 1 wherein said coating is deposited by thermally spraying a powder selected from the group consisting of iron or nickel base alloys containing a noble metal.

3. The electrochemical corrosion potential sensor according to claim 2, wherein the coating is deposited by one of an air plasma spraying and a hyper velocity oxy-fuel technique.

4. An electrochemical corrosion potential sensor according to claim 2 wherein said noble metal is selected from the group consisting of osmium, ruthenium, iridium, rhodium, platinum and palladium.

5. An electrochemical corrosion potential sensor according to claim 4 wherein said noble metal is platinum or palladium.

6. An electrochemical corrosion potential sensor according to claim 5 wherein said sensor tip comprises alloy 42.

7. An electrochemical corrosion potential sensor as claimed in claim 1 wherein said ceramic tip insulating member is sealingly joined to said sensor tip by brazing.

8. An electrochemical corrosion potential sensor as claimed in claim 7, wherein the alloy of the sensor tip comprises an iron-nickel base alloy.

9. An electrochemical corrosion potential sensor as claimed in claim 1, wherein said conductor is a component of a mineral oxide insulated cable having a mineral oxide insulator extending around the conductor.

10. An electrochemical corrosion potential sensor as claimed in claim 9, wherein the mineral oxide insulated cable is joined to the ceramic tip insulating member by a sleeve overlapping the ceramic tip insulating member and the mineral oxide insulated cable.

11. An electrochemical corrosion potential sensor as claimed in claim 10, wherein the sleeve is joined to the ceramic tip insulating member and the mineral oxide insulated cable by brazing.

12. An electrochemical corrosion potential sensor as claimed in claim 10, wherein the ceramic tip insulating member insulates the sensor tip from the sleeve.

13. The electrochemical corrosion potential sensor of claim 10, wherein said sleeve comprises alloy 42.

14. An electrochemical corrosion potential sensor as claimed in claim 1, wherein said noble metal coating is from about 5 to 10 mils in thickness.

15. The electrochemical corrosion potential sensor of claim 1, wherein said stabilized zirconia is one of yttria stabilized zirconia, magnesia stabilized zirconia, and calcia stabilized zirconia.

16. An electrochemical corrosion potential sensor comprising:

- a solid ceramic tip insulating member, said ceramic tip insulating member comprising a stabilized zirconia;
- a sensor tip joined to the ceramic tip insulating member by a braze, said sensor tip comprising an iron-nickel based alloy;
- a coating provided on an outer surface of the sensor tip, said coating comprising at least one noble metal and at least one of an iron-base alloy and a nickel-base alloy; and
- a mineral oxide cable coupled to the ceramic tip member, the mineral oxide insulated cable having a conductor electrically connected to said sensor tip.

17. The electrochemical corrosion potential sensor of claim 16, wherein said stabilized zirconia is one of yttria stabilized zirconia, magnesia stabilized zirconia, and calcia stabilized zirconia.

* * * * *